United States Patent
Freear et al.

(10) Patent No.: US 9,513,258 B2
(45) Date of Patent: Dec. 6, 2016

(54) FAULT DETECTION FOR PIPELINES

(71) Applicant: SPEIR HUNTER LTD., Nottingham (GB)

(72) Inventors: Steven Freear, Manchester (GB); Ben Varcoe, Leeds (GB); David Matthew Joseph Cowell, Shipley (GB); Stephen George Henry Staples, Brough (GB); Chau Vo, Leeds (GB)

(73) Assignee: Speir Hunter Ltd., Nottingham (GB)

( * ) Notice: Subject to any disclaimer, the term of this patent is extended or adjusted under 35 U.S.C. 154(b) by 189 days.

(21) Appl. No.: 14/381,828

(22) PCT Filed: Mar. 1, 2013

(86) PCT No.: PCT/GB2013/050526
§ 371 (c)(1),
(2) Date: Aug. 28, 2014

(87) PCT Pub. No.: WO2013/128212
PCT Pub. Date: Sep. 6, 2013

(65) Prior Publication Data
US 2015/0061659 A1    Mar. 5, 2015

(30) Foreign Application Priority Data
Mar. 2, 2012 (GB) .................................. 1203717.2

(51) Int. Cl.
*G01N 27/72* (2006.01)
*G01N 27/82* (2006.01)
*G01V 3/15* (2006.01)

(52) U.S. Cl.
CPC .............. *G01N 27/72* (2013.01); *G01N 27/82* (2013.01); *G01V 3/15* (2013.01)

(58) Field of Classification Search
CPC ............... G01N 27/72; G01N 27/82–27/9093; G01N 27/20; G01N 27/205
See application file for complete search history.

(56) References Cited

U.S. PATENT DOCUMENTS

| | | | | |
|---|---|---|---|---|
| 4,538,108 A | * | 8/1985 | Huschelrath | G01N 27/82 324/232 |
| 5,479,100 A | * | 12/1995 | Fowler | G01N 27/83 324/220 |

(Continued)

FOREIGN PATENT DOCUMENTS

| | | |
|---|---|---|
| RU | 2264617 C2 | 11/2005 |
| RU | 88453 U1 | 11/2009 |
| WO | 2013019136 A1 | 2/2013 |

OTHER PUBLICATIONS

International Search Report mailed Apr. 24, 2013 for International Patent Application PCT/GB2013/050526 filed Mar. 1, 2013.

(Continued)

*Primary Examiner* — Minh N Tang
*Assistant Examiner* — David Frederiksen
(74) *Attorney, Agent, or Firm* — Maier & Maier, PLLC (57) ABSTRACT

The invention concerns a structural integrity assessment system and method for determining stress concentration zones in a structure, such as a pipeline. The invention comprises a magnetic field sensor array arranged to be moved relative to the structure in a known direction. A controller is provided for recording one or more magnetic field readings taken by the magnetic field sensor array at different locations in the direction of movement thereof. A processor is arranged to identify one or more feature within said values, said feature being indicative of a region of reduced structural integrity in the structure. The processor also receives a data input for a further parameter corresponding to the location of the sensor array and compares the (Continued)

feature with the further parameter in order to verify that said feature corresponds to a region of reduced structural integrity for the structure.

15 Claims, 7 Drawing Sheets

(56) References Cited

U.S. PATENT DOCUMENTS

| | | | | |
|---|---|---|---|---|
| 6,051,977 | A * | 4/2000 | Masuda | G01N 27/205 324/326 |
| 6,888,353 | B1 | 5/2005 | Wiegert | |
| 7,688,072 | B1 | 3/2010 | Wiegert et al. | |
| 8,447,532 | B1 | 5/2013 | Goroshevskiy et al. | |
| 8,542,127 | B1 | 9/2013 | Goroshevskiy et al. | |
| 2003/0169035 | A1* | 9/2003 | Crouzen | G01B 7/28 324/230 |
| 2004/0041560 | A1* | 3/2004 | Walters | G01N 27/82 324/238 |
| 2007/0083398 | A1* | 4/2007 | Ivey | G06Q 40/08 705/4 |
| 2007/0222436 | A1* | 9/2007 | Gao | G01N 27/82 324/220 |
| 2008/0042645 | A1* | 2/2008 | Kaack | G01N 27/87 324/220 |
| 2012/0253696 | A1* | 10/2012 | Pearson | G01N 27/82 702/38 |
| 2013/0027029 | A1 | 1/2013 | Goroshevskiy et al. | |

OTHER PUBLICATIONS

Billings S et al: "Interpretation of high-resolution low-altitude helicopter magnetometer surveys over sites contaminated with unexploded ordnance" Journal of Applied Geophysics, Elsevier, Amsterdam, NL, vol. 72, No. 4. Oct. 6, 2010 (Oct. 6, 2010), pp. 225-231, XP027534465, ISSN: 0926-9851.

M B Rogers et al: "Ground-Based Magnetic Surveys As a New Technique to Locate Subsurface Drainage Pipes: A Case Study", Applied Engineering in Agriculture, vol. 21, No. 3, Jan. 31, 2005 (Jan. 31, 2005), pp. 421-426, XP055060093.

Staples, et al., "Solving the inverse problem of magnetisation—stress resolution", J. Appl. Phys. 113, 133905 (2013); doi: 10.1063/1.4799049. Published by the American Institute of Physics.

D. L. Atherton, "Detection of Anomalous Stresses in Gas Pipelines by Magnetometer Survey 1982", J. Appl. Phys. 53, 8130 (1982); Department of Physics, Queen's University, Kingston, Ontario K7L 3N6, Canada.

Mag613 Submersible Magnetometer Array by Bartington Instruments. http://www.bartington.com/Literaturepdf/Datasheets/Mag613%20DS1854.pdf. Visited Aug. 14, 2014.

http://www.whoi.edu/main/alvin/subsystems/optional-scientific-samplers#3. Visited Aug. 14, 2014 (see Magnetometer).

http://www.polyinform.com/. Visited Aug. 13, 2014.

Francis, et al., "Magnetic Localization of Buried Cable by the Scarab Submersible" (Manuscript received Jun. 19, 1980) American Telephone and Telegraph Company The Bell System Technical Journal vol. 60, No. 4, Apr. 1981.

Szitkar, et al., "Processing and Analysis of Near-Seafloor Magnetic Anomalies around Futuna Island, SW Pacific Ocean", American Geophysical Union, Fall Meeting 2011, abstract #GP41A-0991.

* cited by examiner

FAULT DETECTION FOR PIPELINES

The present invention relates to the detection of faults or otherwise assessing the integrity of structures such as pipelines.

Structural problems with existing pipelines are of significant concern to a pipeline operator. An aging pipeline infrastructure means that such problems are generally becoming more prevalent over time. The cost of excavating and replacing or repairing existing pipeline is considerable, not only due to the cost of the engineering works but also due to the potential need to shut down a pipeline whilst works are carried out.

This problem has been documented in the past and there have been proposed methods to allow pipelines to be inspected such that faults can be detected and maintenance or overhaul work to be scheduled in a manner which minimises the impact for the pipeline operator.

Existing techniques for pipeline inspection involve insertion of an In-Line-Inspection (ILI) tool such as a pipeline inspection gauge (commonly referred to as a 'pig') into the pipeline. Pigs have historically been used for cleaning pipelines but have, more recently, been provided with sensors and associated electronics for detecting faults, such as cracks, corrosion or other geometric defects in the wall of the pipeline. It is also known to use calliper pigs to determine any deviation of the cross-section of the pipe from a desired, circular profile. Such pigs are propelled along the pipeline and record a plurality of measurements along the desired section of pipeline.

Whilst it is possible to insert pigs into pipelines for a number of industries and/or pipelines without stemming the flow along the pipeline, this is not always the case. In addition to the material conveyed by the pipeline, any of the geometry, curvature and/or valves within a pipeline can make pigging impossible. If a pig becomes stuck part way along the pipeline section under inspection, it will require retrieval, which causes further problems for the operator.

Furthermore, and perhaps more importantly, pigging represents an invasive process and risks contamination of the pipeline. Hence, even where pigging is possible, it is generally desirable to minimise the frequency with which any such activity is undertaken.

As an alternative to pigging, Russian Patent RU 2 264 617 discloses a non-invasive system for detecting areas of questionable structural integrity within a pipeline by recording changes in the magnetic field a short distance from the pipeline.

It is an aim of the present invention to provide a method and system for non-invasive assessment of the integrity of a structure, which can offer results having improved accuracy and/or which provides an alternative to the use of pigs.

According to a first aspect of the invention, there is provided a method of assessment of the integrity of a structure comprising: positioning one or more magnetic field sensors at a first location remote form the structure; taking one or more magnetic field readings at the first location and a plurality of further locations spaced from the first location in a known direction; processing the plurality of magnetic field reading values or a plurality of parameter values derived therefrom so as to identify a feature within said values; and outputting an indication of said region of reduced structural integrity.

The method may comprise receiving or recording a further data input indicative of an operational parameter at said first or further locations; verifying that said feature corresponds to the location of a region of reduced structural integrity for the structure based on said further data input; and outputting the indication of said region of reduced structural integrity in dependence upon said verification.

The output may comprise an indication of the location of said region of reduced structural integrity. The indication may be output on a plan, map schematic or other graphical output of the structure.

The present invention is particularly advantageous in that it can improve the accuracy with which a region of questionable structural integrity can be identified and/or located. This allows the invention to be used with greater certainty such that future maintenance or repairs works can be scheduled based on the results attained.

The invention can be used as a predictive tool to assess the nature or severity of an anomaly detected in the structure. The structure may comprise an accessible, buried, or otherwise readily inaccessible structure, such as a pipeline. The known, or first, direction may be aligned with a longitudinal axis of the pipeline.

The method may comprise moving the sensor or instrumentation relative to the structure in the known direction and taking one or more further readings at further locations, at known distance from said first location.

The method may comprise recording the location of said first and/or further locations using a co-ordinate positioning system. The co-ordinate positioning system may comprise a satellite positioning receiver. The method may comprise recording values of latitude and longitude and/or altitude, typically at each location. The method may comprise recording accuracy measurements for each location.

The method may comprise providing a plurality of sensors in an array, the spacing of each sensor in the array being known and/or fixed. The array may comprise three or more sensors aligned along a common axis. The array may comprise a two-dimensional array, having at least two sensors aligned along a first axis and at least two sensors aligned along a further axis, said further axis being perpendicular to the first axis. The array may comprise a three-dimensional array having at least two sensors aligned in each of three perpendicular axes.

The receiving or recording a further data input may comprise recording magnetic field values at a plurality of locations, typically using any one of the sensor arrays defined above, and determining a change in magnetic field values in at least a first and a second direction. The validation may comprise identifying a feature in one of the plurality of directions and identifying a corresponding feature in one or more other (typically linearly independent) directions. The first and second directions may be opposing directions (e.g. to and/or from said first location). The first and second directions may be perpendicular directions. Such a process may be performed for first, second and third directions. Such a process may be performed in respect of three or more directions, such as four, five or six directions, which may comprise any combination of opposing and/or perpendicular directions.

In one embodiment the potential feature may be compared or correlated with the further data input so as to either confirm or deny the presence of said region of reduced structural integrity.

The region of reduced structural integrity may comprise a region of increased or decreased stress in the structure. A level or value or type of stress anomaly in the structure may be determined in dependence upon the plurality of magnetic field reading values or a plurality of parameter values derived therefrom.

The feature may comprise a peak, trough, zero-crossing, or other similar feature in the magnetic field readings, for example from one location to a further location.

The method may comprise measuring an inclination of said one or more magnetic field sensor, typically about one or more axes. The further data input may comprise an angular orientation reading for said sensor at one or more of said locations. The verifying said feature may comprise processing the angular orientation reading and magnetic field reading to determine a magnitude of the magnetic field in the direction of one or more reference axes.

The magnetic field readings may be processed, typically using a computer or other processing means, to determine a gradient in the magnetic field or a derived parameter in said direction. The gradient or derived parameter may be determined in a plurality of directions.

The method may comprise receiving or obtaining survey results for the structure and the verifying that said feature corresponds to a region of reduced structural integrity may comprise comparing said feature and/or its location to one or more regions of reduced structural integrity identified in said survey results. The survey results may comprise ILI survey results.

The method may comprise outputting a numerical value or score indicative of the severity of the structural integrity, for example in dependence upon said verification step. The method may comprise outputting a numerical value or score indicative of the degree of certainty of verification of the structural integrity. The method may comprise outputting an estimated value of internal stress within the structure at said location.

The method may comprise scheduling maintenance or overhaul work for the structure dependent on the outputting an indication of reduced structural integrity. The method may comprise setting operational parameters or limits for the structure dependent on the indication of reduced structural integrity.

The method may comprise outputting one or more graphical or textual displays of the results of the method, such as a map, plan or schematic of the structure indicating the one or more determined locations of reduced structural integrity. The method may comprise outputting a plot or chart of magnetic field strength or a parameter derived therefrom, such as a magnetic field gradient, for example in one or more directions.

According to a second aspect there is provided a method of operation of a pipeline comprising the method of the first aspect.

According to a third aspect of the invention, there is provided a system for assessment of the integrity of a structure corresponding to the first aspect.

According to a fourth aspect of the invention, there is provided a data carrier comprising machine readable instructions for the control of one or more processors to perform the steps of the method of the first aspect.

Any of the preferable features described above with reference to any one aspect may be applied to any further aspect, wherever practicable.

Practicable embodiments of the present invention are described in further detail below by way of example only with reference to the accompanying drawings, of which.

The present invention is derived from the understanding that it is possible to determine an indication of the stress experienced by a structure, such as a pipeline, remotely there-from by measurement of changes in the magnetic field in the vicinity of the structure. This determination can be used to identify regions of high and/or abnormal stress concentration and thereby identify unsafe regions for which further investigation or repair/maintenance works are required.

Figure 1:
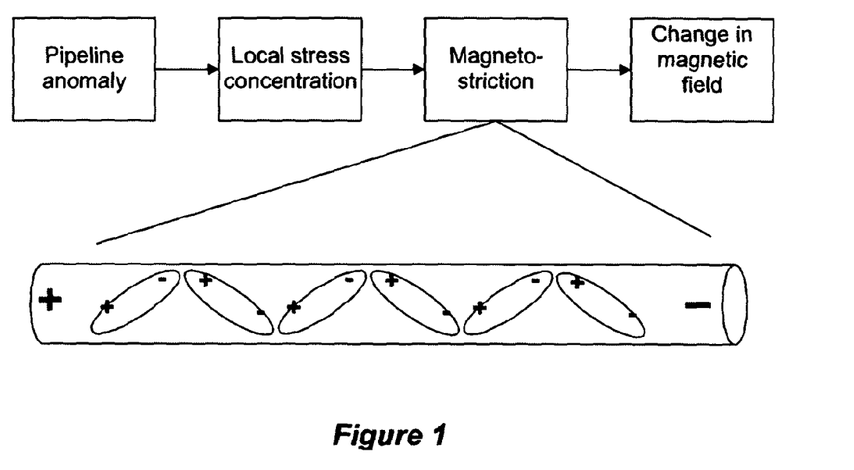
FIG. 1 shows a schematic flow diagram of the occurrence of change in magnetic field surrounding a structure.

Turning firstly to FIG. 1, there is shown a schematic diagram of the steps involved in a change in the condition of a structure leading to a change in the surrounding magnetic field. The present invention is concerned with the occurrence of a geometric or metallurgical (e.g. corrosion) anomaly in a metallic (typically ferromagnetic) structure such as, in this example, in the wall of a pipeline. Such an anomaly may occur due to a particular event or else over a period of time, for example due to movement in the surrounding subsoil; due to cyclic loading by seasonal changes in temperature; and/or due to the pressure/flow regime within the pipeline.

The anomaly in the pipeline leads to a local stress concentration or profile focused about the anomaly. This stress concentration has been found by the inventors to cause a measurable change in the magnetic field surrounding the pipeline according to the inverse magnetostrictive (or Villari) effect. Thus the dipoles within the structure become misaligned from their at-rest state, thereby generating a global or macroscopic magnetisation of the structure in the vicinity of the anomaly. The nature of the resulting magnetic field will vary dependent on the crystal alignment within the structure and the direction of the tensile or compressive loading of the structure.

Field Apparatus

Figure 2:
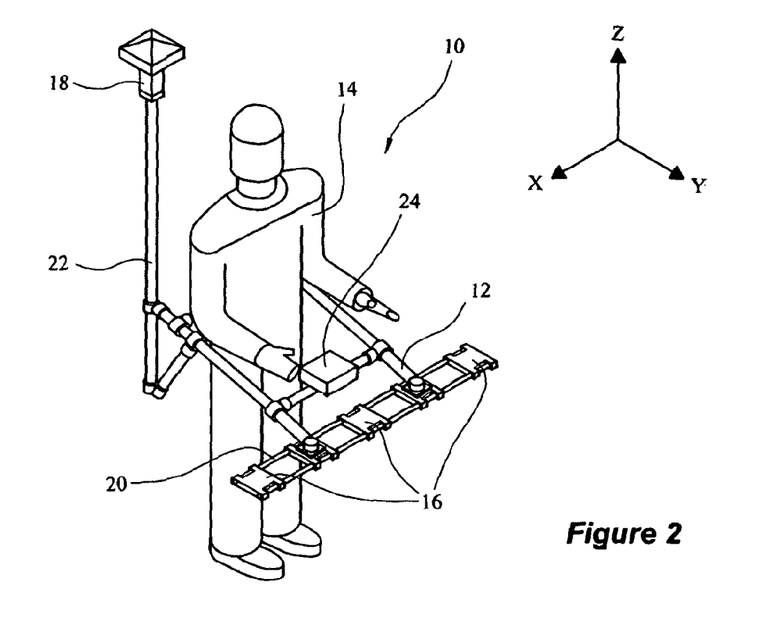
FIG. 2 shows a schematic three-dimensional view of an apparatus for determining a change in magnetic field according to an example of the invention.

An example of equipment 10 used to detect and measure changes in the magnetic field due to the above-described phenomena is shown in FIG. 2. The equipment 10 in this example is arranged to be portable by mounting the relevant instruments to a frame 12 such that the assembly can be carried by an individual 14. The instruments/sensors comprise, in brief, a plurality of magnetic field sensors 16 assembled in a predetermined array, as will be described in further detail below, and a position determining system 18.

The sensors in this embodiment comprise directional or vector magnetometers, such as fluxgate magnetometers, which each measure the magnetic field in the X, Y and Z directions. In this example, the sensors create an analogue voltage output that is proportional to the magnetic field component in each direction. The particular magnetometers selected in this embodiment comprise Three-Axis Fluxgate Magnetic Field Sensors. These magnetometers have been found to have beneficial low noise and low power characteristics, although it may be possible to use other vector magnetometers.

The term "sensor" as used herein may include the use of a plurality or sensors, which may for example be co-located in the form of a sensor device.

The sensors 16 are mounted on one or more rigid spacer arm 20, which may be referred to herein as a sensor arm, such that the relative positions and spacing of the sensors are known and remain fixed during use of the equipment. In this regard, the sensors are mounted onto support blocks which in turn mount onto the sensor arm 20. The sensors in the present embodiment are located in front of the operator. These are located in the left, centre and right hand mounting blocks along the sensor arm 20.

The position determining system comprises a receiver arranged to receive electro-magnetic signals, typically from a plurality of satellites, such that an associated processor can determine the location of the receiver based on the location of the signal transmitters and the time taken for the received signals to reach the receiver. A further support 22 arm is used to maintain the position determining system 18 above the sensors 16 when oriented for use as shown in FIG. 2.

An axis system can be established as shown in FIG. 2, wherein the direction of travel in use is substantially in the Y direction. The apparatus is oriented in use such that the Y direction is substantially parallel with the longitudinal axis of a pipeline being assessed. In this context, the arm 20 and array of sensors 16 extend in a direction (i.e. in the X direction) which is lateral/perpendicular to the direction of travel and/or the longitudinal axis of the pipeline. The sensors 16 in this configuration lie in a substantially horizontal plane. The position determining receiver 18 is maintained in a known spaced relationship with respect to the sensors 16 above the sensors, in the Z direction. In this example, the position determining receiver 18 is also behind, and to the left hand side of the operator 14 and/or the centre of the array of sensors 16.

The frame 12 and the further arm 22 maintain the desired spacing of the sensors and receiver 18 during use of the equipment. This spacing is important since it is used in determining the precise location of the sensors 16.

It is also important that the receiver 18, which comprises electronic equipment is suitably displaced relative to the sensors so as to avoid interference with the magnetic field caused by the pipeline which will typically be below the sensors 16 in use. In addition, the receiver 18 is positioned above the operator to maintain the receivers direct view of the sky.

The arm 20, frame 12 and further arm 22 comprise a support structure that is preferably formed of materials which are transparent with respect to the magnetic field as far as possible. Carbon fibre and/or plastic materials are used to this end. In the particular embodiment of FIG. 2, the support structure is formed of carbon fibre tubes, coupled together using plastic joints. Where metal components are necessary, aluminium is used as far as possible to minimise distortion of the surrounding magnetic field.

Whilst it is apparent from FIG. 2, that the support structure is configured to allow it to be carried or worn by an operator on foot, it is possible according to other embodiments that the support structure could also be arranged for mounting on a vehicle such as a trailer or cart or similar wheeled structure. The carrying of the apparatus on foot is in many ways preferred due to the varying terrain which is often experienced when following the path of a pipeline above ground.

Furthermore, the operator will typically steady him/herself when carrying the apparatus such that the sensors will be maintained substantially in the desired horizontal orientation when taking magnetic field readings. To further guarantee a predictable orientation of the sensors 16, it is possible to provide the support arm 20 and/or structure with one or more orientation indicators, such as a spirit level, such that the operator can confirm or adjust the orientation accordingly. Additionally or alternatively it is possible to provide the support structure with a leveling mechanism, allowing the support arm to pivot with respect to the remainder of the support structure and thereby maintain a desired, substantially horizontal orientation.

Whilst the above support structure embodiments may help to retain the sensors in a predictable orientation, the inventors have determined that the accuracy of the readings can be improved by providing an orientation sensor, such as an inclinometer, to determine the angular orientation of the array with respect to the horizontal and/or vertical axis.

Figure 3:
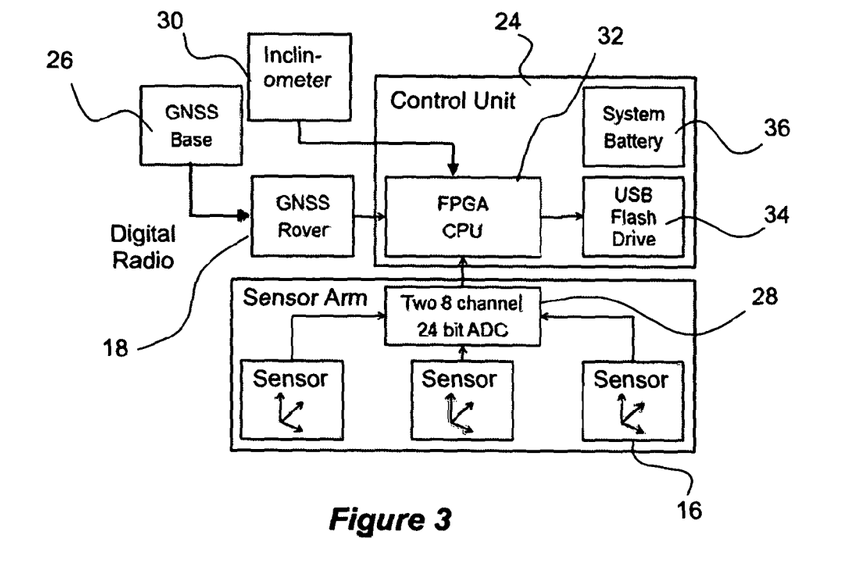
FIG. 3 shows the basic architecture of an apparatus for determining a change in magnetic field according to an example of the invention.

FIG. 3 shows the key components that comprise the electronic system of the apparatus, in order to allow collection of the required data by a control unit 24. The sensors 16 comprise vector magnetometers, each capable of measuring the magnetic field in three dimensions.

The position-determining system comprises the aforementioned receiver 18, which is portable with the apparatus and comprises a high resolution global navigation satellite system (GNSS). Such a system utilises signals from multiple satellite positioning constellations to provide increased accuracy over using a single satellite constellation.

A static base unit 26 is also provided which also comprises a GNSS receiver module. The static base unit functions in the manner of a conventional satellite positioning unit in that it receives a plurality of satellite signals which are used to determine its location. However the fixed nature of the base unit 26 allows a highly accurate position determination for use as a reference point. The base unit 26 calculates and transmits satellite correction data to the mobile receiver 18 such that it can correct its position determination with reference to the base unit 26 in the manner of a so-called Real Time Kinematic (RTK) system. The base unit monitors errors in the received satellite signals and transmits real time corrections to the mobile unit 18, typically over a UHF radio link. In this regard, either unit may have a plurality of antenna. Using this technique, the position determination can be carried out with a relative accuracy between the two receivers of below 1 cm and typically approximately 15 mm.

The receivers also record the raw satellite data so that, should the radio link be lost, corrections can be applied using post processing software.

The inventors have found this accurate positioning capability to be highly beneficial for the location of pipeline anomalies with a greater degree of certainty that can allow meaningful action to be taken in response to those findings.

The system comprises an analogue-to-digital converter (ADC) 28 for digitising the analogue output signal of the magnetometers 16. In this embodiment, nine channels are required to digitise the output of the three magnetometers in each direction. Each ADC is capable of digitising eight signals and thus two ADC chips are used to digitise the outputs from the magnetometers. This also allows some redundancy to accommodate further sensor arrays as will be described in further detail below, although further ADC chips/channels could be added as necessary. The ADCs are preferably selected to offer high resolution and low noise. 24-bit ADCs are used in this embodiment.

Analogue filtering is performed on the magnetometers output before digitisation to remove undesired frequencies, such as, for example, 50 or 60 Hz interference from power lines and/or general electronic noise such as that present due to digital electronics and radio waves. Additional or alternative filtering steps may be used to eliminate background or environmental effects on the magnetic field. Such filtering may allow the invention to be used in a variety of different environments (e.g. at different altitudes, on land, in enclosed spaces and/or underwater).

An inclinometer 30 may be provided in this embodiment to provide real-time indication of the angular orientation of the magnetometer array relative to one or more of the X, Y and/or Z axes. In this embodiment a reading of angular inclination relative to each of those axes is taken. A micro-electromechanical system (MEMS) based inclinometer may be used for this purpose and preferably a precision, triaxial device.

The inclinometer is typically mounted on the sensor arm 20 such that its relative orientation with respect to the magnetic field sensors is fixed.

A control unit 24 is provided on the support structure as shown in FIG. 2, typically on a cross bar or other support formation in front of the user.

The control unit 24 receives and manages the incoming data signals from the magnetometers (via the ADC) as well as the GNSS receiver 18 and, optionally, also the inclinometer output. The control unit 24 comprises one or more processor 32. In this embodiment a Field Programmable Gate Array (FPGA) is used, which provides a flexible, reprogrammable device that is provided with custom digital logic for the purpose of the present invention. Alternatively, the processor 32 could be realised using a dedicated microprocessor integrated circuit.

In the current configuration the FPGA contains two microprocessors and custom real-time digital interface to the ADC chips 28. The first control unit processor is an autonomous processor that receives and interprets data from the satellite positioning system 18. This processor directly interfaces to the main processor so that the satellite positioning parameters are updated in real-time (i.e. without delay, or else wherein any delay is sufficiently small that it would not significantly affect the accuracy of any readings taken for a given location).

The main processor 32 controls or coordinates the entire operation of the instrument 10, with the primary function being to record magnetometer and satellite positioning data to a memory device, typically in real-time. This is achieved by co-ordinating concurrent readings for the magnetic field (typically in all directions) with position data and time stamping a memory entry or record of all those readings. The memory entry may also comprise the current inclinometer reading. Such co-ordinated, time-stamped data capture from all sensors facilitates effective processing of the data at a later time. Since a significant volume of data can be gathered for any single survey, it will be appreciated that the reliability of the data for later processing is of particular importance.

In addition to the main processor 32, the control unit comprises a non-volatile data store 34, which may take the form of a USB Flash drive, and a power source, in the form of a rechargeable battery 36. The control unit preferably also comprises a visual display unit or screen, via which pertinent information can be provided to the operator, such as any, or any combination of, battery life, inclination readings, position information and/or field strength readings.

During use, the operator walks along the path of a, typically buried, pipeline in the Y direction with the sensors 16 oriented and spaced in the X direction as shown. The known, fixed spacing of the sensors 16 is important to note, as will be discussed below.

The parameters recorded by the control unit comprise any, or any combination, of: the X, Y and Z data from each magnetometer (identified in the further figures as parameters X1, Y1, Z1, X2, Y2, Z2, X3, Y3 and Z3); GNSS Date, Time, Longitude, Latitude, Altitude; Satellite Positioning Fix Mode; Number of satellites used for positional computation; Horizontal dilution of precision (HDOP); RMS latitude error [meters]; RMS longitude error [meters]; RMS altitude error [meters]; and Inclination about X, Y and Z axes.

Recording the RMS error of each measurement provides confidence in the absolute position of each magnetic field measurement, which data is not available from single receiver GNSS systems. As the data is saved to the USB Flash device, error checking information is appended to each data record so that any data corruption can be detected at a later time and the corrupted data record can be subsequently removed.

Additionally, the main processor outputs positional and status information to the control unit display.

In embodiments which include an inclinometer system, the instantaneous angle of the sensors is determined, which may also be time stamped and recorded in the manner described above.

Magnetic Field Sensor Arrays

Figure 4:
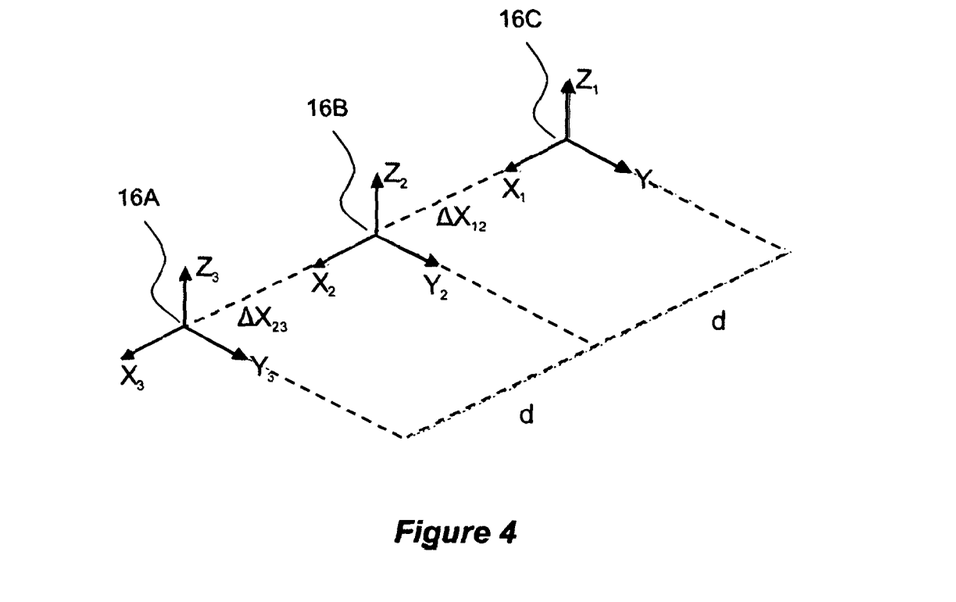
FIG. 4 shows a sensor array according to a first example of the invention.

FIG. 4 shows the arrangement of magnetic field sensors shown in FIG. 2 for detecting the direction and strength/magnitude of the external magnetic field. Accordingly each sensor is a three-dimensional sensor in that it can record the magnitude of the magnetic field in the X, Y and Z directions.

In this embodiment, three such sensors 16A, 16B and 16C are provided in a linear array. The sensors 16A, B and C are aligned with respect to the X axis, such that the Y and Z axes are perpendicular to the linear array of sensors. Each of the sensors is spaced from the adjacent sensor by an equal, fixed distance, 'd'.

This arrangement of sensors is used to determine the rate of change of the magnetic field in the X direction, which typically represents a lateral direction across the pipeline, when the Y axis is the direction of travel along the pipeline. However it will be appreciated that the array of FIG. 4 could alternatively be oriented in the Y or Z axes if the rate of change in those axes is required. Whilst it will be noted that a minimum of two sensors could be used to measure a gradient, the inventors have determined that the use of three sensors provides beneficial results as will be described below.

Further embodiments of sensor arrays in accordance with the invention are described with reference to FIG. 5. In one such embodiment a further sensor 16D is provided, which is spaced by the same distance, 'd', from one of the sensors 16A, B or C. Ideally the sensor 16D is adjacent the middle sensors 16B. However, unlike the linear array of FIG. 4, the further sensor 16D is spaced from the other sensors in the Y direction. Thus the combined sensors 16A-D now define a two-dimensional, or planar, array extending in the XY plane.

The known, fixed distance between the sensors 16D and 16B allows a corresponding magnetic field gradients (i.e. for all three axes) to be determined in the Y direction.

Whilst sensor 16D is provide in the positive Y direction (i.e. in the direction of travel), it could also be provided in the negative Y direction (i.e. behind or trailing the array 16A-C). Additionally a further sensor 16D could be provided in both the positive and negative Y directions with respect to sensor 16B so as to define a three sensor linear array extending in the Y direction.

In another embodiment, further sensor 16E is provided, which is spaced by the same distance, 'd', from one of the sensors 16A, B or C. Ideally the sensor 16E is adjacent the middle sensors 16B. However, unlike the linear array of FIG. 4, the further sensor 16D is spaced from the other sensors in the Z (typically substantially vertical) direction. Thus the combined sensors 16A-C and E now define a two-dimensional, or planar, array extending in the XZ plane.

The known, fixed distance between the sensors 16E and 16B allows a corresponding magnetic field gradients (i.e. for all three axes) to be determined in the Z direction.

Whilst sensor 16E is provide in the positive Z direction (i.e. upwards), it could also be provided in the negative Z direction (i.e. downwards). Additionally a further sensor 16E could be provided in both the positive and negative Z directions with respect to sensor 16B so as to define a three sensor linear array extending in the Z direction.

Figure 5:
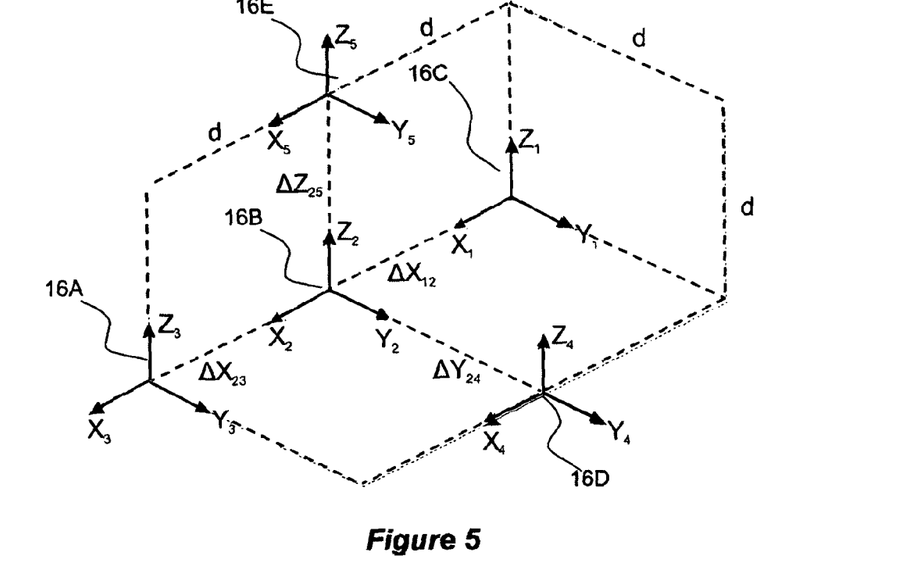
FIG. 5 shows a sensor array according to a second example of the invention.

As shown in FIG. 5, further sensors 16D (in the Y direction) and 16E (in the Z direction) are provided so as to provide a three-dimensional array, in which each sensor is spaced from an adjacent sensor by an equal distance in either of the X, Y or Z axes. As described above, such an arrangement could be supplemented with further sensors in the negative Y and Z directions.

Whilst the above embodiments can provide up to three sensors aligned in each axis/direction, it is to be noted that further sensors could be provided in any or all of those directions to improve the accuracy of gradient determination and/or identify any spurious sensor readings.

In one embodiment, the field strength for each sensor is recorded such that the gradient between all the individual sensors of the array can be determined. Additionally or alternatively, the gradients between the individual sensors may be recorded by the control unit. The gradient between sensor 16A and 16B is determined by calculating the difference in sensor readings, $\Delta X_{23}$, and dividing by distance 'd' to give the change per unit length. This process of gradient determination can be repeated for all the sensors in the array, including values $\Delta X_{23}$, $\Delta X_{12}$, $\Delta Y_{24}$ and $\Delta Z_{25}$ in the example of FIG. 5.

Anomaly Identification

The magnetic field and position readings are taken at a rate of between approximately 20 and 50 Hz. If it is assumed that the operator moves in the direction of the pipeline at a rate of approximately 1 m/s, then this results in readings at approximately 2-5 cm intervals along the length of the pipeline. However it will be appreciated that by simple adjustment of the sample rate or speed of travel, readings could be taken with spacing of anywhere between 0.5 and 50 cm. Whilst it is entirely possible to take data readings at finer length intervals, the added potential accuracy is offset against the size of the resulting data set and the additional processing power required to generate the results. It is to be noted in this regard that time stamping of the satellite positioning data can be achieved up to 100 Hz, thereby accommodating further accuracy or quicker travel speeds as necessary.

The sensors in the array each provide an output for the total magnetic field which comprises a component representing the Earth's magnetic field and an additional, variable component corresponding to the variations in the pipeline under inspection. For a reading of the Earth's magnetic field typically in the region of 30 to 60 µT, the additional component due to the pipeline can be expected to have a magnitude in the region of a few, such as, for example between 0-5 or 10, µT.

Figure 6:
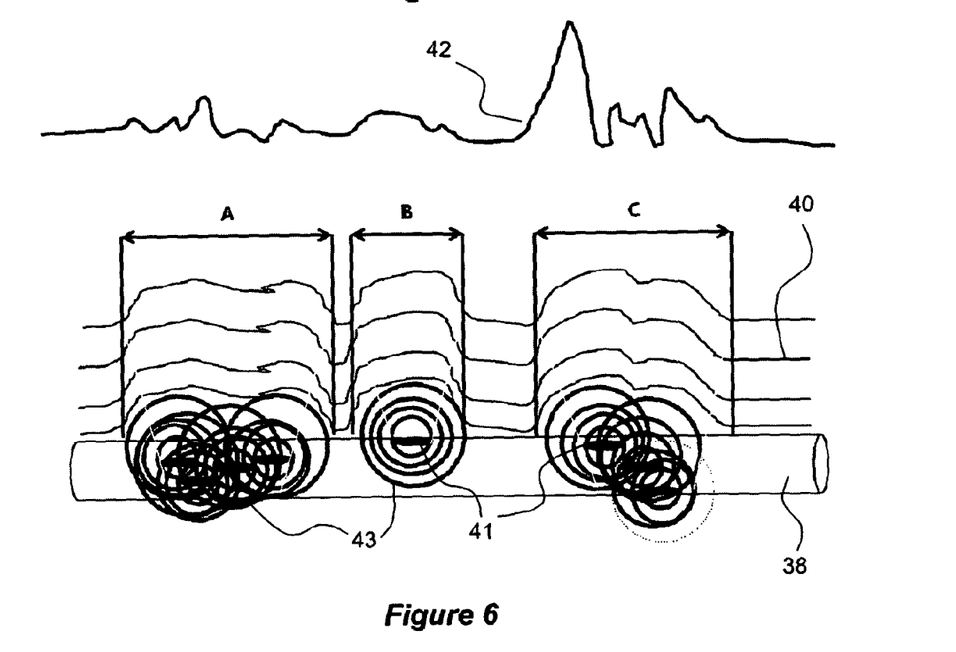
FIG. 6 shows a schematic of an example of results obtained according to one example of the present invention.

The magnetic field measurements and/or gradient values can be plotted along the length of the pipeline 38. FIG. 6 shows schematically the changes or disturbances in the magnetic field 40 that are produced by individual, or a plurality of, anomalies A, B and C in the pipeline structure. As described above, those anomalies correspond to regions of stress in the pipeline structure, whereby the magnetic flux leakage emanating from a stress concentration zone under applied conditions of stress can be modeled in accordance with the theory of magnetostriction. The plot 42 of magnetic field variations thus shows changes in magnetic field which correspond to the location of the anomalies 41. Thus the degree of stress experienced by the pipeline is deduced from the characteristics of the magnetic field along/across the pipeline structure.

As can be seen in FIG. 6, the magnetic field spreads or dissipates with distance from the anomaly 41. This dissipation of the magnetic field disturbances occurs in three dimensions, i.e. over the surface of a sphere having a radius equal to the distance from the anomaly, which is represented as a series of concentric circles 43 in FIG. 6. Thus a correction factor can be applied to the disturbances recorded in the magnetic field at a distance from the anomaly in order to more closely identify the anomaly. A correction factor may be estimated or accurately determined based on a known or estimated depth of the pipeline and/or the magnetic permeability of the medium between the pipe and the sensors.

Depending on the processing power available within the control unit, data processing may be conducted locally whilst magnetic field measurements are being recorded, or with a slight delay thereafter. However in the present embodiment, the recorded data is processed later or remotely using a computer running one or more modules of machine-readable code as will be described below with reference to FIG. 7. The software system imports the data files produced by the instrument and then performs data analysis to allow visualisation and post-processing of the results.

Figure 7:
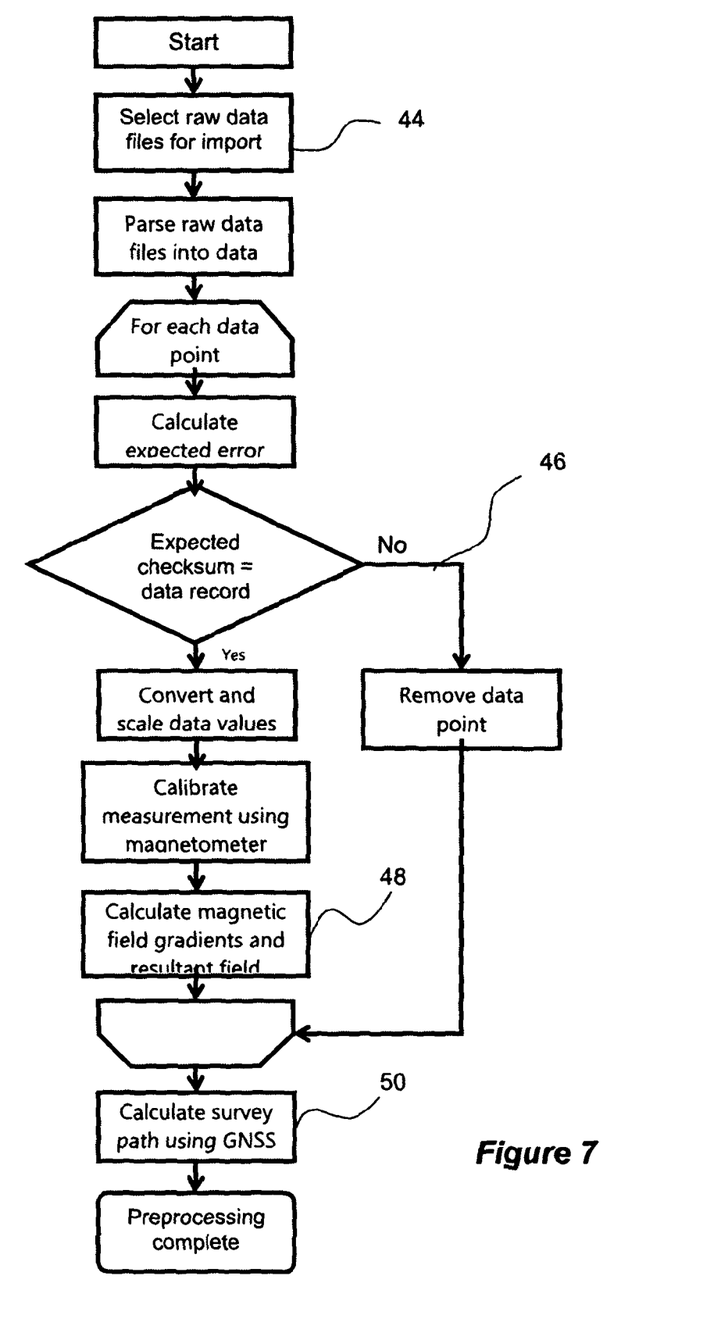
FIG. 7 shows a flow diagram of data handling steps performed according to an example of the invention.

At step 44 in FIG. 7 the software suite selects and processes the raw data files created by the instrument by parsing the raw data files into the computer memory in order to place the data into a predefined data structure for interrogation.

The software also determines an expected count or summation of data entries and checks each data entry against the expected value within an iterative loop 46. Erroneous data entries are removed and for the retained data entries, the magnetic field sensor readings are converted to standard, recognised units. In this case the sensors readings are converted and scaled to SI derived units of magnetic flux density in Tesla. The determined value is also modified using a calibration factor that is applied based on magnetometer calibration data, such as a calibration chart, which may be predetermined for each sensor either before and/or after field readings are taken.

Once calibrated, the software then calculates the magnetic field gradients at step 48 according to the differences between adjacent sensors readings in the manner described above. In this calculation, it will be appreciated that the Earth's magnetic field, which is substantially constant, cancels out, thus leaving the relative variation between the sensors in the array. At this point the software can also determine the resultant field (i.e. magnitude and direction) based on the components recorded in each direction by the sensors.

In the event that an inclinometer is used, the angle of the sensor array relative to the X, Y and/or Z axes will be known and a correction is applied at 48 to the magnetic field values in each direction to compensate for any variations in orientation at the time the sensor readings were taken. When perfectly aligned, the Y axis will be aligned with the longitudinal axis of the pipeline and the X axis will be horizontal and thus any offset from these values can be determined by the inclinometer, possibly in conjunction with a direction of travel derived from the satellite positioning data. If any angle of offset is known the resultant magnetic field magnitude in the direction of the X, Y and Z axes can be determined prior to calculation of the gradients and the overall resultant filed.

In this regard, the inclination data may be considered to be used in a further calibration step and can compensate for the walking movement of the operator, operator error, variations in terrain, etc.

Whilst the terms a "horizontal" and "vertical" are used above in relation to the sensor orientation, it will be appreciated that those terms relate to a situation in which it is assumed that the pipeline runs in a substantially horizontal direction. If gradients (i.e.

variations in depth relative to the ground's surface) of the pipeline are known, then true alignment with respect to the inclination of the pipeline can be determined, which may vary with respect to a horizontal and/or vertical alignment.

The extra calibration/compensation process(es) can increase confidence and accuracy in the raw recorded data and eliminate a majority of false detection of pipeline anomalies.

At stage 50, the survey path is calculated based on the GNSS data recorded.

Figure 9:
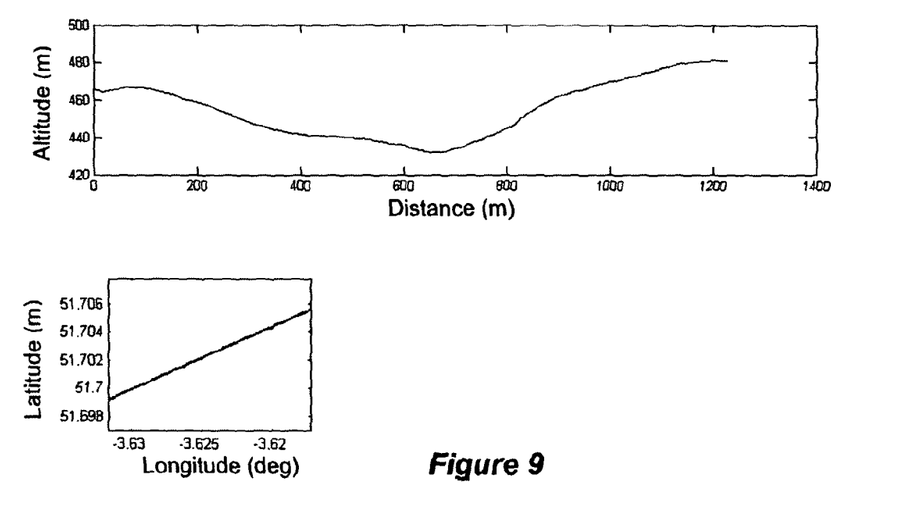
FIG. 9 shows plots of position data for a pipeline recorded according to one example of the invention.

Using the above-determined information, a significant number of 2D or 3D graphical outputs, such as plots can be generated and displayed to a user on screen or saved/printed using conventional computing means. FIG. 9 shows the different two-dimensional plots of location which may be produced, on or against which pipeline anomaly information may be provided.

In particular, the raw data (absolute field, gradient and/or resultant field) can be output as a graphic for display in any combination of 2D and/or 3D plots showing:
Data vs distance along survey route, or
Data vs any combination of Latitude, Longitude and Altitude.

Whilst such plots in themselves can hold significant value for the pipeline operator, the invention can offer improved automation of anomaly detection and/or improved accuracy of anomaly detection/quantification according to the following processes.

The software can process the data described in relation to FIG. 7 by automatically identifying features in the data indicative of anomalies. In one embodiment, such features are identified by setting a threshold value of magnetic field gradient. Thus the software can step through the data entries and identify anomalies based on locations at which the gradient meets or exceeds the threshold value. Such thresholding may be applied to the raw data sets.

In one example, the user may set the threshold value, for example based on experience, such that it is above the background fluctuations in the magnetic data. Alternatively, the software may run a routine in order to assess data and apply probability distribution parameters thereto, for example by assuming a Gaussian distribution and assigning values of mean and standard deviation to best approximate the actual distribution of the data. The software can thus automatically set a threshold to identify only a portion of the results in which the highest gradient values are achieved.

The centre of any peaks or local maxima (e.g. spikes) in the absolute gradient and/or resultant fields along the length of the pipeline above the threshold can thus be defined as anomaly locations. In one embodiment, a location of a peak in the magnetic field may be compared by the software the gradient data to determine whether there is a maxima in magnitude of the gradient on either side of said location. Such comparisons can serve to qualify the finding of a supposed anomaly.

In an alternative or additional embodiment, the software runs a validation routine upon determination of a potential anomaly (i.e. based on peaks in the gradient or resultant field data discussed above) by checking one or more further parameters associated with the potential anomaly.

In this regard, the provision of three sensors, for example in a linear array, as described in relation to FIGS. 4 and 5, is particularly beneficial in that the software can determine the gradient from a first sensor, 16B, in opposing directions by determining a first gradient in the direction of one adjacent sensor, 16A, and a second gradient in the direction of the other adjacent sensor, 16C. The calculation of two X-axis gradients has been found to allow determination of whether a converging or diverging magnetic field across the pipeline is present. This determination can be used to greatly improve the assessment of an anomaly by acknowledging, for example, convergence of the field from opposing directions onto a common location.

Whilst this method provides an increased accuracy of determination using sensors in a linear array, the method can additionally or alternatively use the sensors of two or three-dimensional arrays to validate suspected anomalies.

For example, by using the sensors in the Y-direction, the Y-axis gradient can be calculated for the vicinity of the suspected anomaly in order to determine whether there is the presence/absence of a peak (i.e. a convergence/divergence) or else another feature in the gradient surrounding the suspected anomaly. This process may be substituted or repeated to determine whether a corresponding feature exists in the Z-direction using the sensors aligned in the Z axis.

Thus if a corresponding feature is detected in either or both of the Y and Z directions, a location of stress concentration can be identified with greater certainty than has been hitherto possible.

It is to be noted, that in this context, a feature to be identified in the gradient or magnetic field data is not limited only to peaks (i.e. maxima and/or minima) in the data. With reference to FIG. 8, it can be seen that corresponding features can manifest themselves in different forms in varying directions.

Figure 8A:
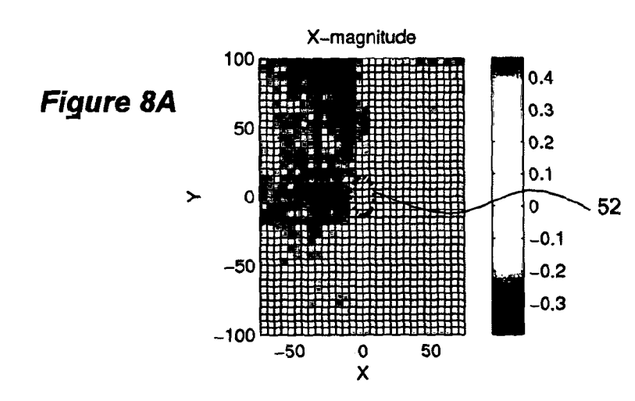
FIGS. 8A to 8D show plots of magnetic field gradient in different directions in the vicinity of an anomaly.
Figure 8B:
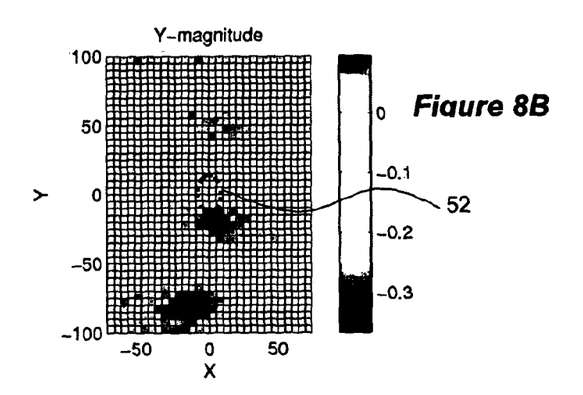
Figure 8C:
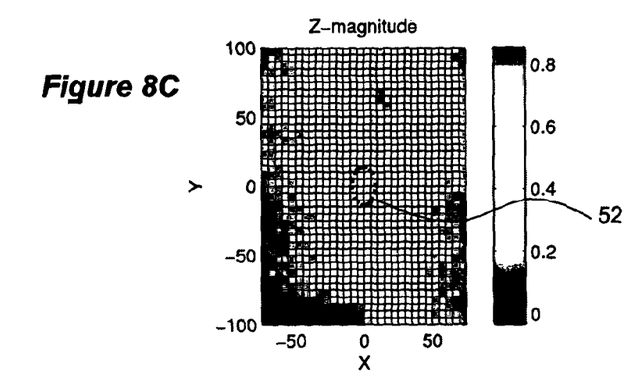
Figure 8D:
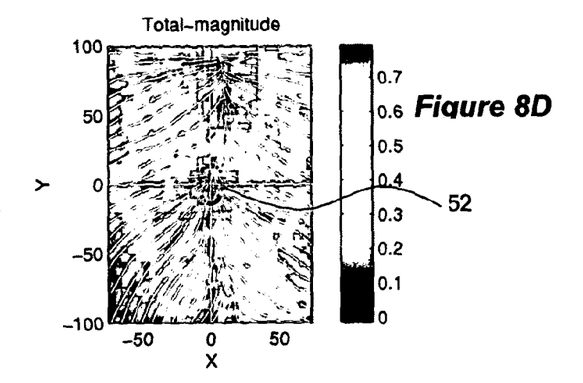

FIGS. 8A-C represent plots of magnitude in the X, Y and Z directions for a test case comprising a length of pipe having a known, substantially symmetrical, anomaly provided in the upper side of the pipe, the outline of which is marked at 52, about the point 0,0 in each plot. In FIG. 8A, it can be seen that the magnitude in a first direction varies from a negative to a positive value as it passes through the known anomaly. Thus in that direction, the location of the anomaly can be identified by the point at which the magnitude crosses or is equal to zero, i.e. a zero-crossing, which can be considered to represent a feature in the context of the invention.

In the plot of FIG. 8B, the corresponding feature can be identified as a point/peak of minimum negative value which is flanked on either side by regions of maximum negative value. Accordingly the corresponding feature in this direction may be defined as a minimum negative value or else a point between two negative peaks.

In the plot of FIG. 8C, the feature can itself be identified as a peak, such that the maxima or centre of the peak can be recorded as the centre of the anomaly. A similar assessment of the corresponding feature can be made in the resultant magnitude plot of FIG. 8D.

Other features dependent on the type and positioning of an anomaly relative to the circumference of a pipe may comprise inflections, troughs, step-changes (e.g. a steep gradient between local maximum and minimum values) or the like. Thus any such observable relationships in the absolute, gradient and/or resultant magnetic fields along the pipeline axis, across the pipeline and/or above the pipeline can be used as feature combinations to determine or verify the presence of a stress-related anomaly.

Developments of this process of searching for features in sets of readings have lead to the provision of automated searching tools based on mathematical models for magnetic flux leakage (i.e. changes in the magnetic field) caused by stress concentration zones in the pipeline material. This is achieved by generating a two dimensional expression for the magnetisation density for a stress concentration zone in terms of geometry (i.e. length and depth in 2-D), assuming the elastic strain reaches a maximum value at the centre of the defect. Using this value of magnetisation density, the total magnetic leakage in the perpendicular directions of a two-dimensional system for different distances in the x and y directions. Accordingly, such modeling steps allow a family of waveforms to be plotted to capture the different changes in the magnetic field that can occur in the x and y directions for varying distances from the stress concentration zone and also for different dimensions of stress concentration zone itself. This family of waveforms can then be used to define the set of features in the magnetic field measurements that are considered to be indicative of stress concentration zones and/or potential defects in a pipeline.

In an additional or alternative embodiment, a continuous wavelet transform may be used to define the range of features in the sensor readings to be identified and stress concentration zones. For example the mathematically modeled wave forms representing stress concentration zones can be processed to assess the variations that may occur due to changes in scale (time/distance) and magnitude (value). Thus the attributed variations in a common mother waveform can be identified in the sensor data that has been regularly sampled.

A search routine can then be established to identify the presence of such waveforms in the data derived from the magnetic field sensor readings. A feature detected in one direction can be cross-referenced with a feature determined in another direction at the same location to automatically confirm the presence of a stress concentration zone without the need for manual inspection of the sensor readings. This presents a particularly powerful and quick system for detecting anomalies in a submerged or buried structure using non-invasive sensing techniques.

In the manner described above converging or diverging magnetic fields will be detected along the pipeline in one or more directions, typically in the X and/or Y directions, using the various arrays of sensors described above. The location of a zero vertical, Z-axis, gradient may also be used to indicate vertical magnetic field lines, thereby indicating a concentration of the field on an anomaly. Accordingly, the multi-directional or multi-dimensional gradient data made possible by embodiments of the invention will allow the user to ignore background magnetic anomalies (which may not manifest themselves in multiple corresponding features in different directions) and more accurately locate pipeline anomalies.

Once correctly identified, the locations of the identified stress concentrations in the pipeline can be determined based on the corresponding location information stored against the relevant data entry by the control unit. The anomaly locations can be output as markers on a display of the raw data.

The magnitude of the recordings can also be used to correlate to the magnitude of the stress concentration at the anomaly. This can provide a direct, numerical correlation to the severity of the anomaly or the determination of the actual stress.

Additionally or alternatively, in further embodiments of the invention, the type of anomaly may be identified by the varying features in different directions/axes, whereby, for example a hoop-stress induced anomaly may comprise a different combination of features to that of say a bending moment in the pipeline, which may in turn differ from an indentation or stress caused by a unidirectional, point load on the pipeline. Thus the present invention may allow for qualitative as well as quantitative assessment of the anomaly, which can in turn allow diagnosis of a cause of the anomaly and the proposition of likely required maintenance or overhaul work needed to reduce to operational risk posed by the anomaly.

Figure 10:
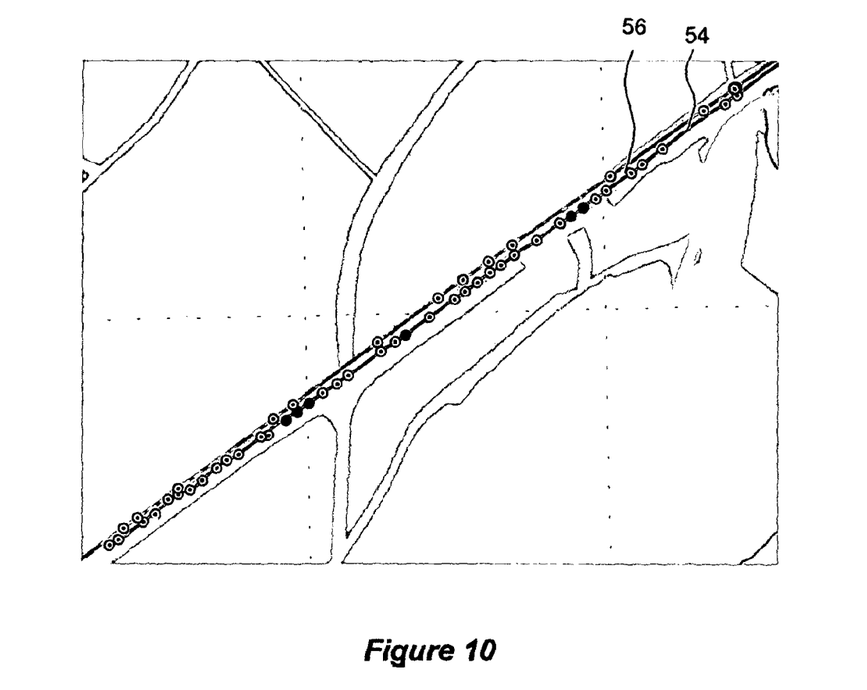
FIG. 10 shows a graphical output of a pipeline surveyed in accordance with an example of the invention.

The anomaly locations and survey route can be automatically shown, for example as an overlay, on satellite photographs or maps of the survey site as shown in FIG. 10. The route is shown by line 54 and the markers are identified at 54. Those markers in this embodiment are colour coded to provide a representation of severity. However, as described above, a significant volume of additional information could be provided to the user by way of a graphical or textual output in relation to each anomaly else for the whole region being surveyed. Corresponding outputs or reports including numerical indication of the level of stress can also be output based on the above discussed data.

Correlation of Results and Stress Modeling

In pipelines for which existing survey results are available from use of ILI tools, the results generated by any of the above-described embodiments can be compared to corresponding ILI results. This comparison of results obtained using two fundamentally-different techniques provides the operator with a highly accurate and validated assessment of the structural integrity of a pipeline. The numerical output, such as the ratings, determined by the remote magnetic field sensors can be combined with the output of ILI results to give a total risk rating.

In a more sophisticated embodiment, a user or the software could compare features identified by the present embodiments with corresponding features in existing ILI data.

Fuzzy logic algorithms can be constructed to automate the assessment of any of the embodiments described above or else the combined ILI and magnetometer readings to determine further attributes of a region of questionable structural integrity.

Certain features in existing pipeline are conventionally recorded during installation or later works, such as joins/welds between pipeline sections and the location of valves or other fixtures. Such data provides alternative sources of feature locations, which can be checked against any findings made using the techniques of the present invention in order to validate or discard findings of stress concentration zones in a manner similar to the above-discussed ILI results.

Also, as field surveys are performed and magnetic field characteristics are correlated with anomalies detected by physical inspection, whether internal, external, automated or manual, further relationships between each magnetic field measurement and anomaly characteristics will be established. A database linking magnetic field characteristics and anomaly properties can thus be populated. Such a database will serve to assist a trained operator to detect and characterise pipeline anomalies.

It is proposed that automated software algorithms, possibly using fuzzy logic, will be created where by the observed magnetic fields will be compared against the database linking magnetic field properties and anomaly characteristics.

Figure 11:
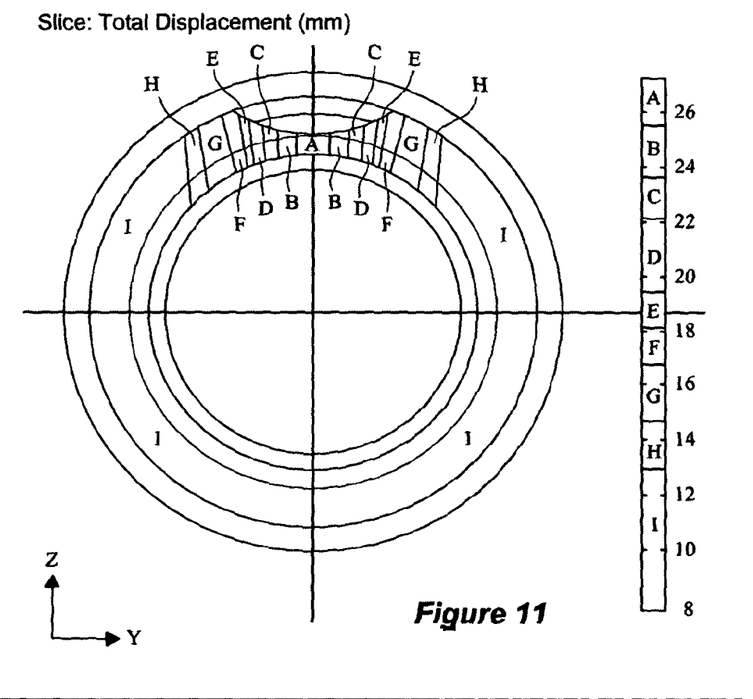
FIG. 11 shows an example of a graphical output of a stress model of a structural anomaly determined as an output of the invention; and, FIG. 12 shows a detailed three-dimensional view of a model of the magnetic field in the vicinity of the anomaly of FIG. 11.
Figure 12:
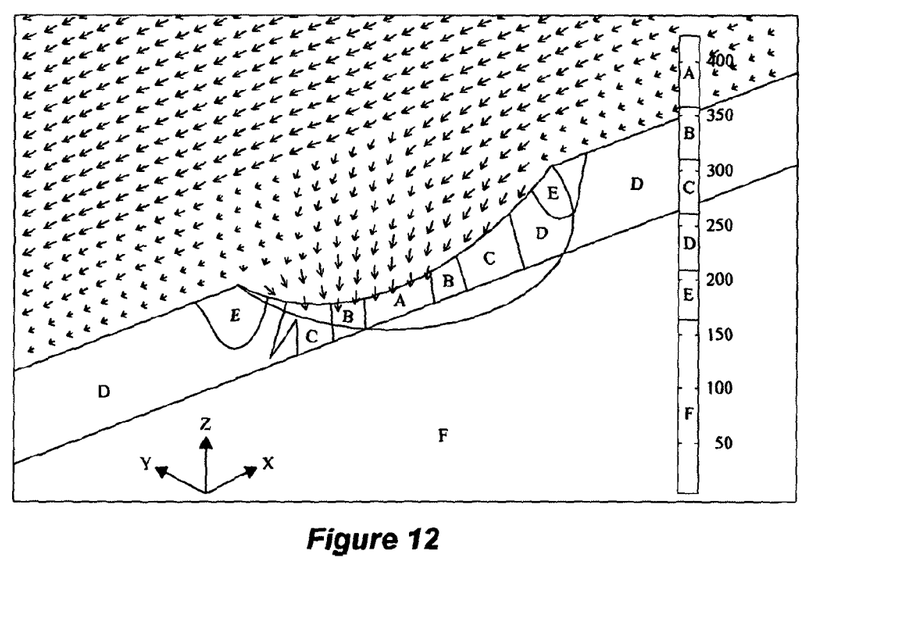

In FIGS. 11 and 12 there is shown the outputs of stress modeling tools, for which the results of the above described surveys can be provided as inputs into a model of a structure, such as a pipeline. Models, varying in complexity from a one-dimensional model along the pipeline, to a two dimensional cross-section or longitudinal section, and/or a three dimensional stress model can be configured using the results of the present invention. In this regard, a model for the structure is typically defined using suitable CAD tools and a mesh is applied to the model such that physical properties of the model are calculated from cell to cell of the mesh, each cell representing a fraction of the area or volume of the material making up the structure of the model.

Stress is determined based on the geometry and physical parameters of the model. In this manner the effect of the anomaly through the structure can be modeled and outputs of displacement or stress or strain through the structure can be generated. The modeling tool then calculates the magnetic field created due to stress-magnetisation or magnetostriction. The model calculates the magnetic field at any point in the model, whether within or surrounding the structure, as shown in FIG. 12. Correlation of magnetic field to the stress concentration in the manner described above and can be fed into the model as boundary conditions.

Using the above described techniques, the pipeline operator can not only identify the location of structural issues but also obtain a quantitative and/or qualitative understanding of the issue. This leads to more effective assessment of safety issues and the possibility of scheduling maintenance or repair work with greater certainty and greater efficiency so as to provide minimal disturbance to the operation of the pipeline.

The above described invention has lead to improved methods for non-invasively locating stress concentration zones in structures. The inventors and Applicant have coined the phrase "Stress Concentration Tomography" (SCT) to refer to such methods.

The invention claimed is:

1. A method of assessment of the integrity of a structure comprising:
positioning one or more magnetic field sensors at a first location spaced from the structure;
taking two or more magnetic field readings at the first location;
taking two or more magnetic field readings at one or more further locations spaced from the structure;
processing the plurality of magnetic field reading values to identify a feature within said values, said feature being indicative of a region of reduced structural integrity in the structure; and,
outputting an indication of said region of reduced structural integrity in dependence upon the feature,
wherein the feature is a magnetic field gradient detected in a first direction and is automatically cross-referenced with a further magnetic field gradient determined in a further direction at the same location to confirm the presence of said region of reduced structural integrity.

2. A method according to claim 1, further comprising:
receiving a data input for a further parameter at the at least one of said first and further location;
verifying that said feature corresponds to the location of a region of reduced structural integrity for the structure based on said further data input.

3. A method according to claim 2, wherein:
identifying the feature within the values comprises determining a change in the magnetic field in the first direction;
the receiving the data input comprises receiving magnetic field readings in at least one of a second and third direction, and
verifying that the change in magnetic field in the first direction corresponds to a region of reduced structural integrity by identifying the further feature in the magnetic field in the at least one of second and third direction at said location.

4. A method according to claim 2, wherein the outputting of said indication comprises outputting an indication of the location of said region of reduced structural integrity in dependence upon said verification.

5. A method according to claim 1, further comprising taking a plurality of substantially concurrent magnetic field readings at the first and further locations, the plurality of field readings comprising magnetic field readings in different directions.

6. A method according to claim 1, further comprising providing a plurality of sensors in an array, the spacing of each sensor in the array being fixed and taking substantially concurrent magnetic field readings with each sensor at the first and further location.

7. A method according to claim 6, wherein the array has three or more sensors.

8. A method according to claim 1, wherein the feature comprises a change in magnetic field value or gradient at or beyond a predetermined threshold, wherein the predetermined threshold is one of a peak, trough, zero-crossing, inflection and step change in magnetic field readings.

9. A method according to claim 1, wherein the processing comprises:
running a search algorithm to automatically determine features in a plurality of directions;
comparing the location of said features in the first direction with the location of features in the one or more further direction; and
outputting an indication of said region of reduced structural integrity when said locations match.

10. A method according to claim 1, further comprising receiving survey results for the structure and verifying that said feature corresponds to the location of a region of reduced structural integrity identified in said survey results.

11. A method according to claim 1, further comprising outputting one of a numerical value or score indicative of severity of reduced structural integrity in dependence upon one of more of a magnitude and rate of change of magnetic field reading values.

12. A method according to claim 1, further comprising scheduling repair work for the structure dependent on the indication of reduced structural integrity.

13. A method according to claim 1, further comprising setting one of operational parameters or limits for the structure dependent on the indication of reduced structural integrity.

14. A system for assessment of the integrity of a remote structure comprising:
- a magnetic field sensor array arranged to be moved relative to a structure in a known direction;
- a controller for recording two or more magnetic field readings taken by the magnetic field sensor array at different locations in the direction of movement thereof;
- one or more processors for processing the two or more of magnetic field readings so as to identify one or more features within said magnetic field readings, said one or more features being a magnetic field gradient indicative of a region of reduced structural integrity in the structure;
- said processor arranged to receive a data input for a further parameter corresponding to the location of the magnetic sensor array and to compare the one or more magnetic field gradients with the further parameter in order to verify that said one or more magnetic field gradients correspond to a region of reduced structural integrity for the structure.

15. A data carrier comprising non transitory machine readable instructions for the control of one or more processors to:
- receive magnetic field sensor readings for a plurality of known locations relative to a structure under assessment;
- search the magnetic field readings to identify features within said values, said features being magnetic field gradients indicative of a region of reduced structural integrity in the structure;
- receive a data input for a further parameter corresponding to the plurality of known locations and to compare the magnetic field gradients with the further parameter in order to verify that said magnetic field gradients correspond to a region of reduced structural integrity for the structure; and
- output an indication of said region of reduced structural integrity in dependence upon said verification.

* * * * *